United States Patent [19]

Ueno et al.

[11] Patent Number: 5,221,799

[45] Date of Patent: Jun. 22, 1993

[54] NEW 15-DEHYDROXY-16-OXOPROSTAGLANDINS

[75] Inventors: Ryuji Ueno; Tomio Oda, both of Hyogo, Japan

[73] Assignee: K.K. Ueno Seiyaku Oyo Kenkyujo, Osaka, Japan

[21] Appl. No.: 921,719

[22] Filed: Jul. 30, 1992

Related U.S. Application Data

[63] Continuation-in-part of Ser. No. 660,833, Feb. 26, 1991, abandoned.

[30] Foreign Application Priority Data

Feb. 26, 1990 [JP] Japan .................................. 2-46932
Sep. 11, 1990 [JP] Japan ................................. 2-241938

[51] Int. Cl.⁵ ............................................. C07C 177/00
[52] U.S. Cl. .................................... 560/121; 562/503
[58] Field of Search ........................ 560/121; 562/503

[56] References Cited

U.S. PATENT DOCUMENTS 4,170,709 10/1979 Kao et al. .......................... 560/121
4,841,091 6/1989 Tanaka .............................. 558/441

FOREIGN PATENT DOCUMENTS 444844 9/1991 European Pat. Off. .......... 560/121

OTHER PUBLICATIONS

Pirillo, IL Farmaco-Ed Sc 31 468 (1976).
Tetrahedron Letters No. 30, pp. 2563-2566.
STN File Server, Abstract No. 43270f.
Chemical Abstracts, vol. 90, 22371g (1979).

*Primary Examiner*—Robert Gerstl
*Attorney, Agent, or Firm*—Sughrue, Mion, Zinn, Macpeak & Seas

[57] ABSTRACT

A compound of the formula:

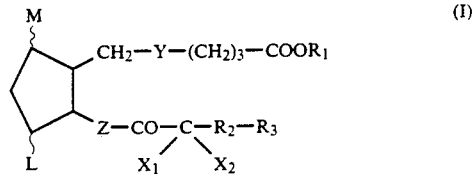

wherein

L and M are hydrogen atom, hydroxy, lower alkyl, hydroxy(lower)alkyl or oxo, provided that at least one of L and M is not hydrogen atom and that the five-membered ring may have one double bond. . . . and when one of L and M is hydrogen atom and the other L and M is oxo, then the five-membered ring has one double bond.

$X_1$ and $X_2$ are hydrogen atom, halogen atom or lower alkyl,

Y is $-CH_2-CH_2-$, $-CH=CH-$, $-C\equiv C-$ or $-CO-CH_2-$,

Z is $-CH_2-CH_2-CH_2-$, $-CH=CH-CH_2$ or $-CH_2-CH=CH-$,

R is hydrogen atom, lower alkyl, lower cycloalkyl, monocyclic aryl, monocyclic aryl(lower)alkyl or monocyclic aroyl(lower)alkyl, $R_2$ is single bond or lower alkylene, $R_3$ is lower alkyl which is unsubstituted or substituted with halogen, lower cycloalkyl which is unsubstituted or substituted with lower alkyl, monocyclic aryl which is unsubstituted or substituted with halogen or halo(lower)alkyl, or monocyclic aryloxy which is unsubstituted or substituted with halogen or halo(lower)alkyl, or a pharmaceutically acceptable salt when $R_1$ is hydrogen atom.

14 Claims, No Drawings

NEW 15-DEHYDROXY-16-OXOPROSTAGLANDINS

This is a continuation-in-part of application Ser. No. 07/660,833 filed Feb. 26, 1991, now abandoned.

BACKGROUND OF THE INVENTION

1. Field of the Invention

The present invention relates to a new prostaglandin compounds and more particularly new 15-dehydroxy-16-oxoprostaglandins.

Prostaglandins (hereinafter, prostaglandin is referred to as PG) are members of a class of organic carboxylic acids that are contained in human and most other mammalian tissues or organs and that exhibit a wide range of physiological activities. Naturally occurring PGs possess as a common structural feature the prostanoic acid skeleton:

$$\text{(A)}$$

Some synthetic analogues have somewhat modified skeletons. On the basis of the structural features of their five-membered ring moiety, the PGs are classified into PGAs, PGBs, PGCs, PGDs, PGEs, PGFs, PGGs, PGHs, PGIs and PGJs. These are further classified based on whether or not there are unsaturated groups and oxidized groups in the chain moiety as:

Subscript 1 - - - 13,14-unsaturated-15-OH
Subscript 2 - - - 5,6— and 13,14-diunsaturated-15-OH
Subscript 3 - - - 5,6- 13,14- and 17,18-triunsaturated-15-OH In the above formula (A), for example, PGEs are compounds which have an oxo group at position 9 and a hydroxy group at position 11. PGFs are compounds which have hydroxy groups at positions 9 and 11. PGDs are compounds which have a hydroxy group at position 9 and an oxo group at position 11. PGAs are compound which have an oxo group at position 9, a hydrogen atom at position 11 and a double bond between positions 10 and 11. It has been known that PGs have various physiological activities such as anti-ulcerous, uterine-contractile, intestine-contractile, vasodilating, and diarrheic activities.

It is also known that the natural PGs are chemically unstable and very rapidly metabolized in the living body.

Compounds having an oxo group in place of a hydroxy group at position 15 of the prostanoic acid skeleton and their derivatives have also been described (for example, JP-A-52753/1989, JP-A-104040/1989 and JP-A-151552/1989).

While the fact that a compound has various activities appears to be advantageous at first sight, the presence of activities which are not useful in individual cases is not desirous because they are disliked as side-effects. Therefore, it is desirous to develop compounds having only one particular activity or a limited number of activities out of various activities of PGs. Furthermore, there is a continuous demand for the compounds of this kind which have improved chemical stability and reduced rate of metabolic degradation in the living body in comparison with the natural PGs. The compounds according to the invention have been successfully synthesized as a result of extensive study seeking for such compounds.

SUMMARY OF THE INVENTION

The present invention provides a compound of the formula:

$$\text{(I)}$$

wherein

L and M are hydrogen atom, hydroxy, lower alkyl, hydroxy(lower)alkyl or oxo, provided that at least one of L and M is not hydrogen atom and that the five-membered ring may have one double bond, and when one of L and M is hydrogen atom and the other of L and M is oxo, then the five-membered ring has one double bond $X_1$ and $X_2$ are hydrogen atom, halogen atom or lower alkyl, Y is $-CH_2-CH_2-$, $-CH=CH-$, $-C\equiv C-$ or $-CO-CH_2-$, Z is $-CH_2-CH_2-CH_2-$, $-CH=CH-CH_2-$ or $-CH_2-CH=CH-$, $R_1$ is hydrogen atom, lower alkyl, lower cycloalkyl, monocyclic aryl, monocyclic aryl(lower)alkyl or monocyclic aroyl(lower)alkyl, $R_2$ is single bond or lower alkylene, $R_3$ is lower alkyl which is unsubstituted or substituted with halogen, lower cycloalkyl which is unsubstituted or substituted with lower alkyl, monocyclic aryl which is unsubstituted or substituted with halogen or halo(lower)alkyl, or monocyclic aryloxy which is unsubstituted or substituted with halogen or halo(lower)alkyl, or a pharmaceutically acceptable salt when $R_1$ is hydrogen atom.

DETAILED DESCRIPTION OF THE INVENTION

In the above formula, the term "halogen" or "halo" denotes fluoro, chloro, bromo and iodo.

It is preferred that the group $-CH=CH-$ in Y has cis configuration and the groups $-CH=CH-CH_2-$ and $-CH_2-CH=CH-$ in Z have trans configuration.

The term "lower" is intended to include a group having 1 to 6 carbon atoms unless otherwise specified.

The term "lower alkyl" as a group or a moiety of hydroxy(lower)alkyl, monocyclic aryl(lower)alkyl, monocyclic aroyl(lower)alkyl or halo(lower)alkyl includes saturated and straight or branched chain hydrocarbon radicals containing 1 to 6, preferably 1 to 5 and more preferable 1 to 4 carbon atoms, such as methyl, ethyl, propyl, isopropyl, butyl, isobutyl, t-butyl, pentyl and hexyl.

The term "lower alkylene" refers to the group obtainable by removing a hydrogen atom from the lower alkyl group as defined above and includes, e.g., methylene, ethylene, propylene, tetramethylene, 2-methyltetramethylene, pentamethylene, hexamethylene, etc.

The term "lowercycloalkyl" refers to a cyclic group formed by cyclization of a lower alkyl group having 3 or more carbon atoms and includes, for example, cyclopropyl, cyclobutyl, cyclopentyl and cyclohexyl.

The term "halo(lower) alkyl" refers to lower alkyl group as defined above which is substituted with at least one and preferably 1 to 3 halogen atoms as defined above and includes for example, chloromethyl, bromomethyl, fluoromethyl, trifluoromethyl, 1,2-dichloromethyl, 1,2,2-trichloroethyl, chloropropyl, chlorobutyl, chloropentyl, chlorohexyl, etc.

The term "hydroxy(lower)alkyl" refers to lower alkyl as defined above which is substituted with at least one hydroxy group, such as hydroxymethyl, 1-hydroxyethyl, 2-hydroxyethyl and 1-methyl-1-hydroxyethyl.

The term "monocyclic aryl" includes phenyl unsubstituted or substituted with lower alkyl substituent, for example phenyl, tolyl, xylyl, cumenyl etc.

The term "monocyclic aryloxy" refers to a group consisting of monocyclic aryl as defined above and bivalent oxygen —O— combined together, and includes, for example, phenoxy, tolyloxy, xylyloxy, cumenyloxy etc.

The term "monocyclic aryl(lower)alkyl" refers to a group consisting of monocyclic aryl and lower alkyl, both as defined above, combined together, and includes, for example, benzyl, phenethyl, tolylmethyl, etc.

The term "monocyclic aroyl(lower)alkyl" refers to a group consisting of monocyclic aroyl such as benzoyl unsubstituted or substituted with lower alkyl substituent and lower alkyl as defined above combined together, and includes phenacyl(benzoylmethyl), toluoylmethyl, xyloylmethyl, etc.

Suitable "pharmaceutically acceptable salt" includes conventional non-toxic salt, and may be a salt with an inorganic base, for example a metal salt such as an alkali metal salt (e.g., sodium salt, potassium salt, etc.) and an alkaline earth metal salt (e.g., calcium salt, magnesium salt, etc.), ammonium salt, a salt with an organic base, for example, an amine salt (e.g., methylamine salt, dimethylamine salt, cyclohexylamine salt, benzylamine salt, piperidine salt, ethylenediamine salt, ethanolamine salt, diethanolamine salt, triethanolamine salt, tris(hydroxymethylamino)ethane salt, monomethylmonoethanolamine salt, procaine salt, caffeine salt, etc.), a basic amino acid salt (e.g., arginine salt, lysine salt, etc), tetraalkylammonium salt and the like. These salts can be prepared by the conventional process, for example by use of the corresponding acid and base or by salt exchange.

The configuration of the ring and α- and/or ω-chain in the above formula (I) may be the same as or different from that in the natural prostaglandins. However, the present invention also include a mixture of a compound having natural configuration and that of unnatural configuration.

In the compounds of the present invention, when the bonds between 13-, 14- and 15-positions are saturated, a keto-hemiketal equilibrium may sometimes be formed by the formation of a hemiketal between the hydroxy group at 11-position and the keto group at 16-position.

When these tautomeric isomers are present, the ratio of the existing isomers will vary depending on the structure of other part of the molecule or the kind of possible substituents and in some cases one of the isomers is predominantly present. The present invention, however, includes both isomers, and while any compound of the invention may be represented by a structure or nomenclature of keto-type, this should be understood as a matter of mere convenience and should not be considered to be intended to exclude the compound in hemiketal type isomer.

In the present invention, individual tautomeric isomers, a mixture thereof, or optical isomers, a mixture thereof, racemic mixture and other isomers such as stereoisomers can be used for the same purpose.

Nomenclature

Nomenclature of 15-dehydroxy-16-oxo-PG compounds herein uses the numbering system of prostanoic acid represented by the formula (A) shown above.

While the formula (A) shows the basic skeleton having twenty carbon atoms, the compounds used in the present invention are not limited to those having the same number of carbon atoms. The carbon atoms in the Formula (A) are numbered 2 to 7 on the α-chain starting towards the five membered ring from the α-carbon atom adjacent to the carboxylic carbon atom which is numbered 1, 8 to 12 on the fine membered ring in the formula (A) starting from the carbon atom on which the α-chain is attached, and 13 to 20 on the ω-chain starting counterclockwise from the carbon atom adjacent of the ring. When the number of the carbon atoms is decreased in the α-chain, the number is deleted in order starting from position 2 and when the number of the carbon atoms is increased in the α-chain, compounds are named as substituted derivatives having respective substituents in place of carboxy group (C-1) at position 2. Similarly, when the number of the carbon atoms is decreased in the ω-chain, the number is deleted in order starting from position 20 and when the number of the carbon atoms is increased in the ω-chain, compounds are named as substituted derivatives having respective substituents at position 20. Stereochemistry of the compounds is the same as that of the above formulas (A) and (B) unless otherwise specified.

Thus, 16-oxo-PGs having 10 carbon atoms in the ω-chain are named as 16-oxo-20-ethyl-PGs.

The above formula, expresses a specific configuration which is the most typical one, and in this specification compounds having such a configuration are expressed without any specific indication about it.

Although PGDs, PGEs and PGFs generally refer to compounds having a hydroxy group at position 9 and-/or 11 of the prostanoic acid nucleus, definition of the 16-oxoprostaglandin compounds in the present invention is extended to include compounds having another group at position 9 and/or 11. Such compounds are named as 9-dehydroxy-9-substituted or 11-dehydroxy-11-substituted compounds.

As stated above, nomenclature of 15-keto-PG compounds is based upon the prostanoic acid. These compounds, however, can also be named according to the IUPAC naming system. Some examples of the both nomenclature are shown in Examples.

The compounds of the invention can be prepared by processes shown in the following Schemes, wherein $P_1$, $P_2$, $P_3$, $P_4$, $P_5$, $P_6$, $P_7$, $P_8$, $P_9$, $P_{10}$, $P_{11}$ and $P_{12}$ are each protective group, A is a leaving group, Y' is —CH=CH—, L' is lower alkyl, $R_1'$ is lower alkyl or monocyclic aryl(lower)alkyl, and $X_1$, $X_2$, $R_2$ and $R_3$ are the same as defined above.

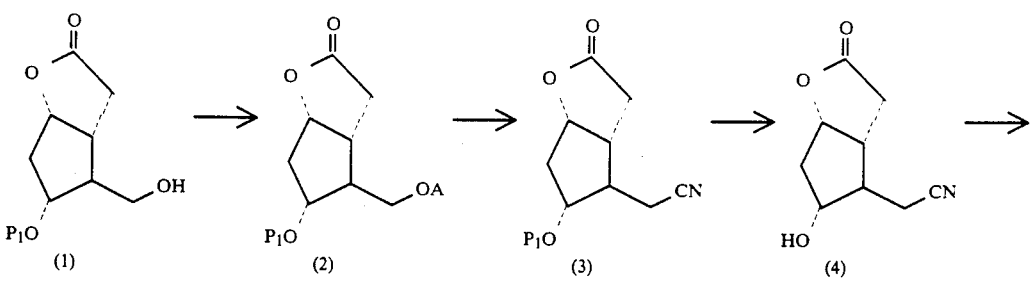
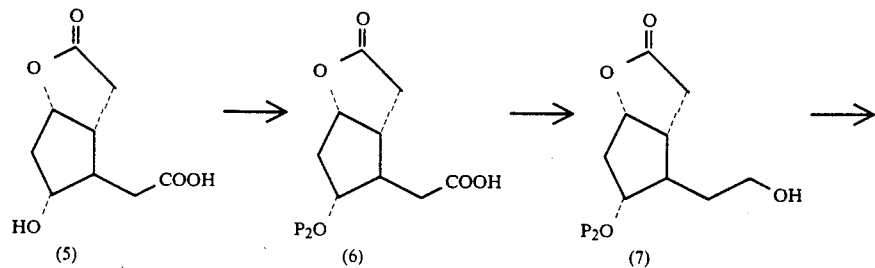
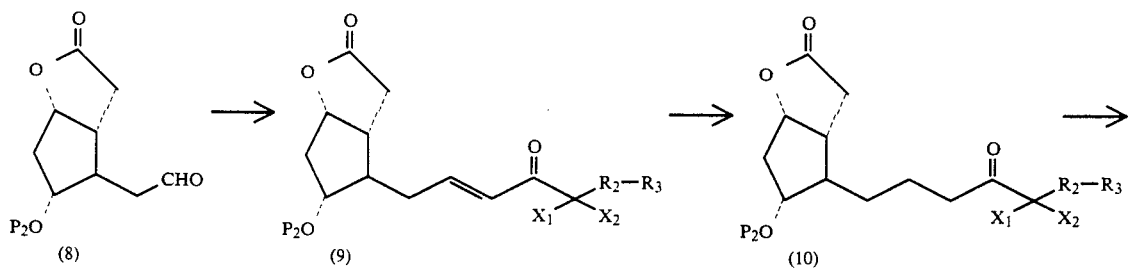
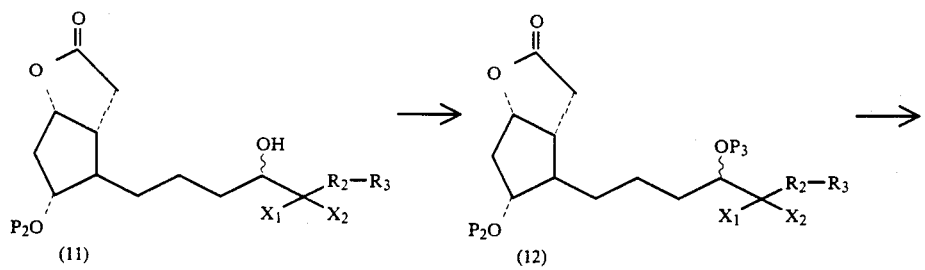
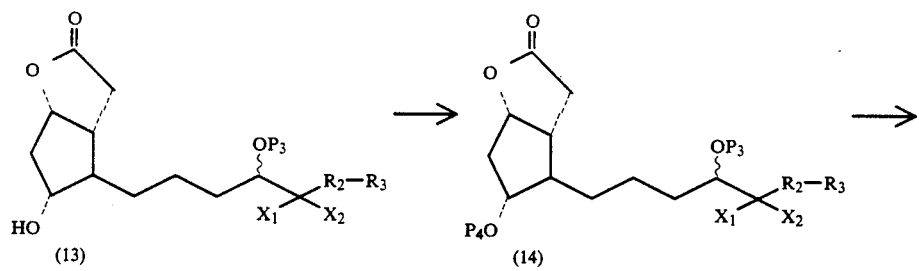
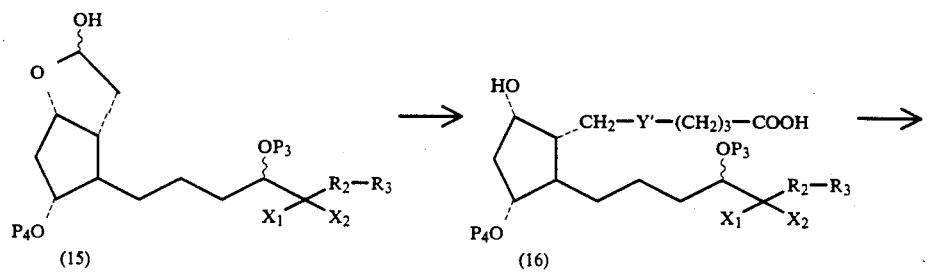

-continued
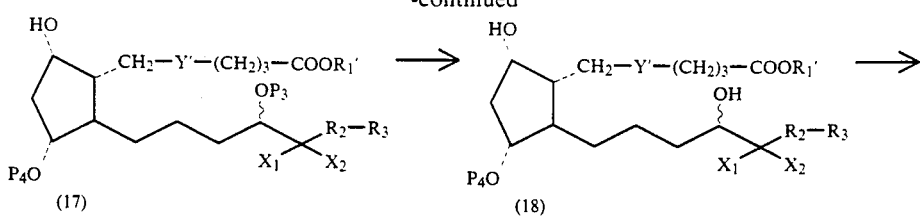
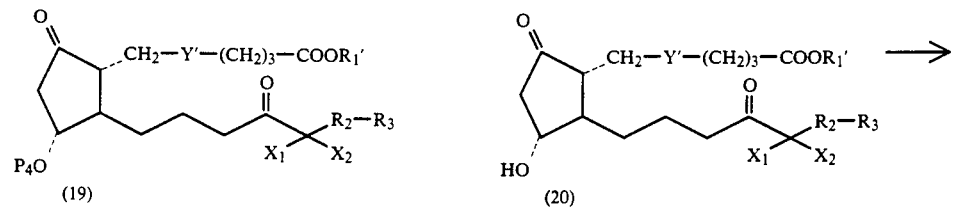
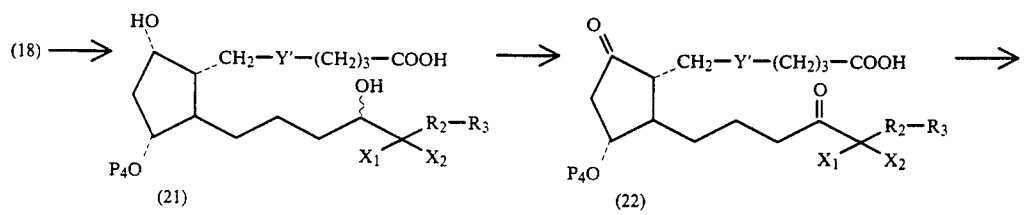
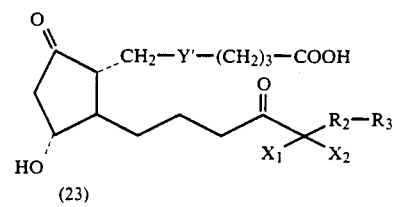
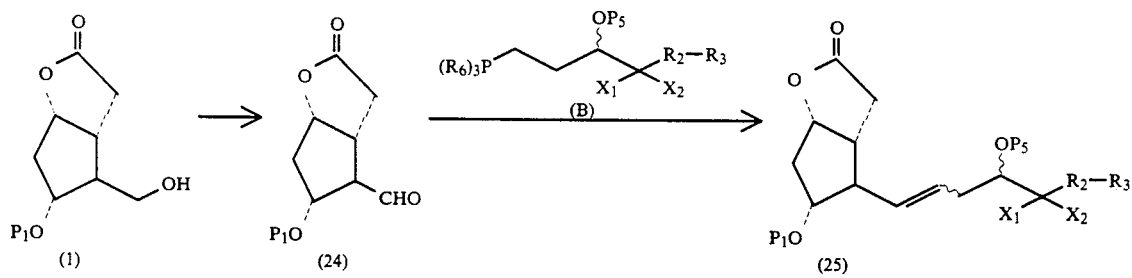
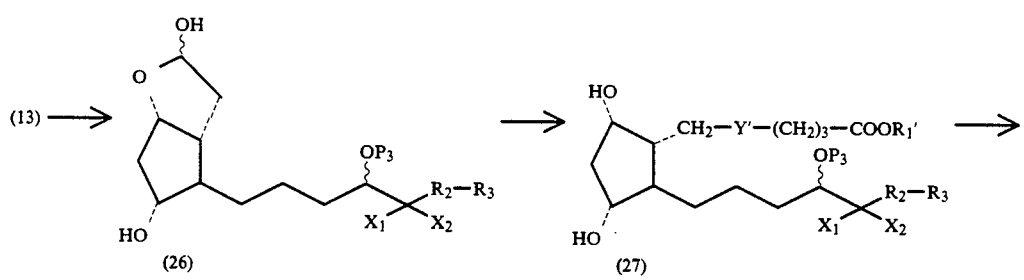
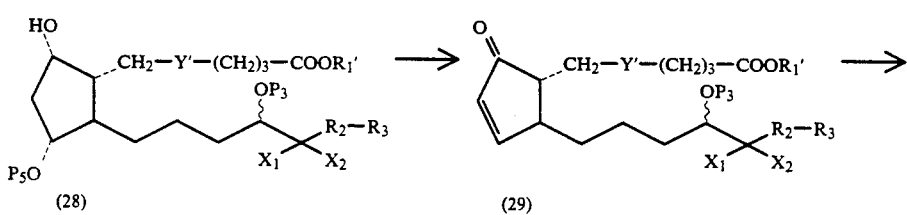

-continued
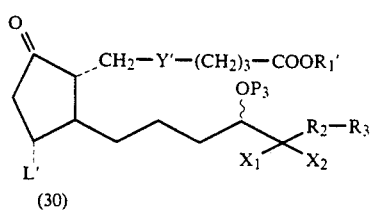
(30)
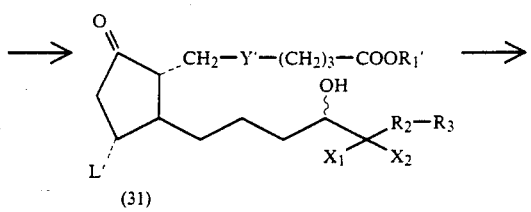
(31)
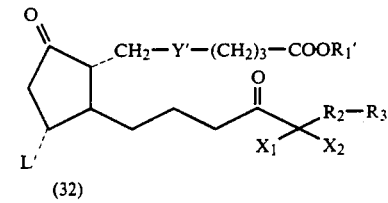
(32)
(18) →
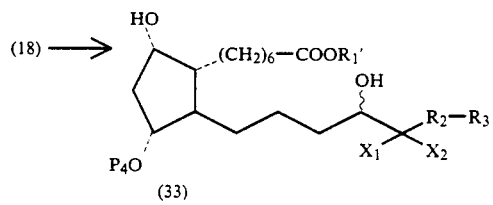
(33)
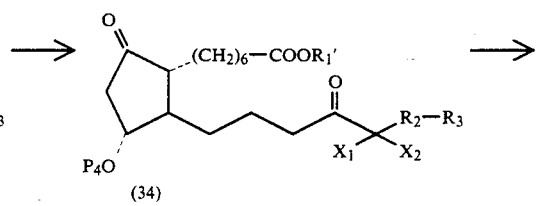
(34)
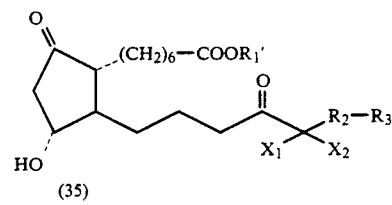
(35)
(13) →
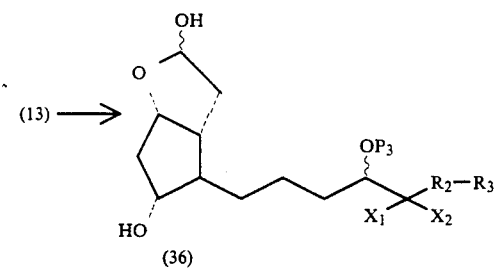
(36)
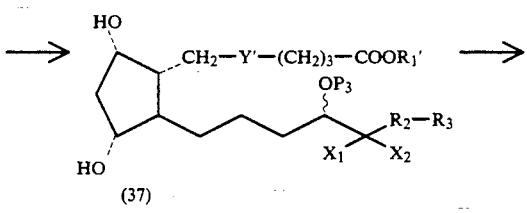
(37)
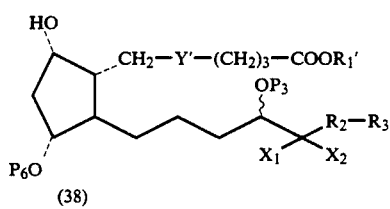
(38)
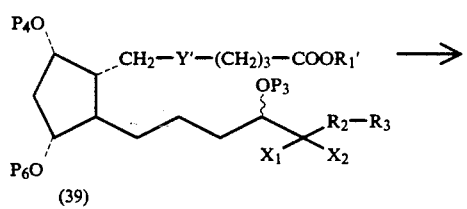
(39)
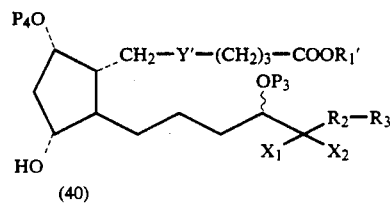
(40)
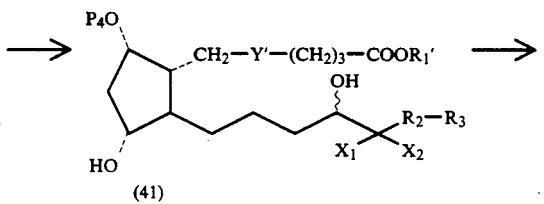
(41)

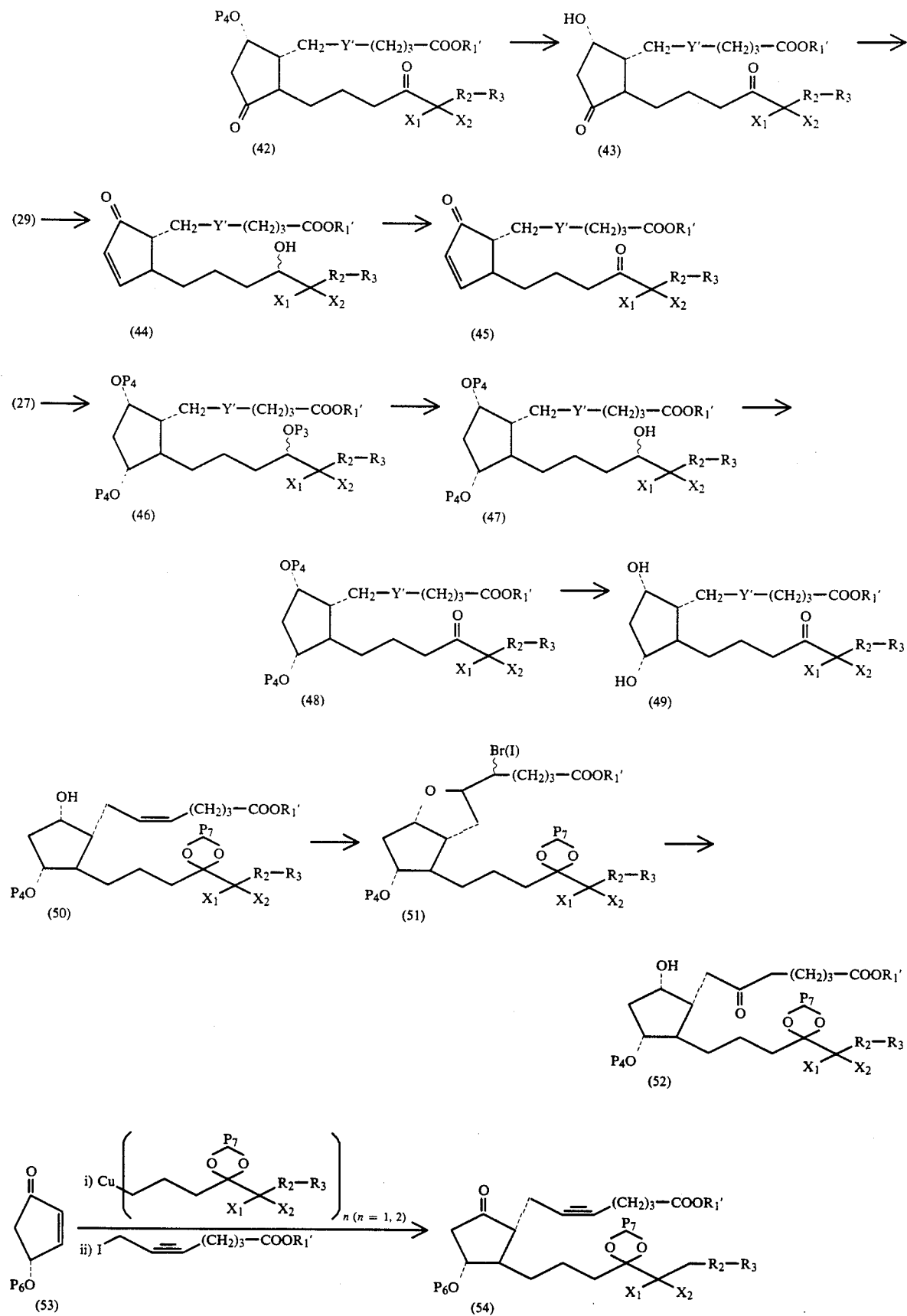

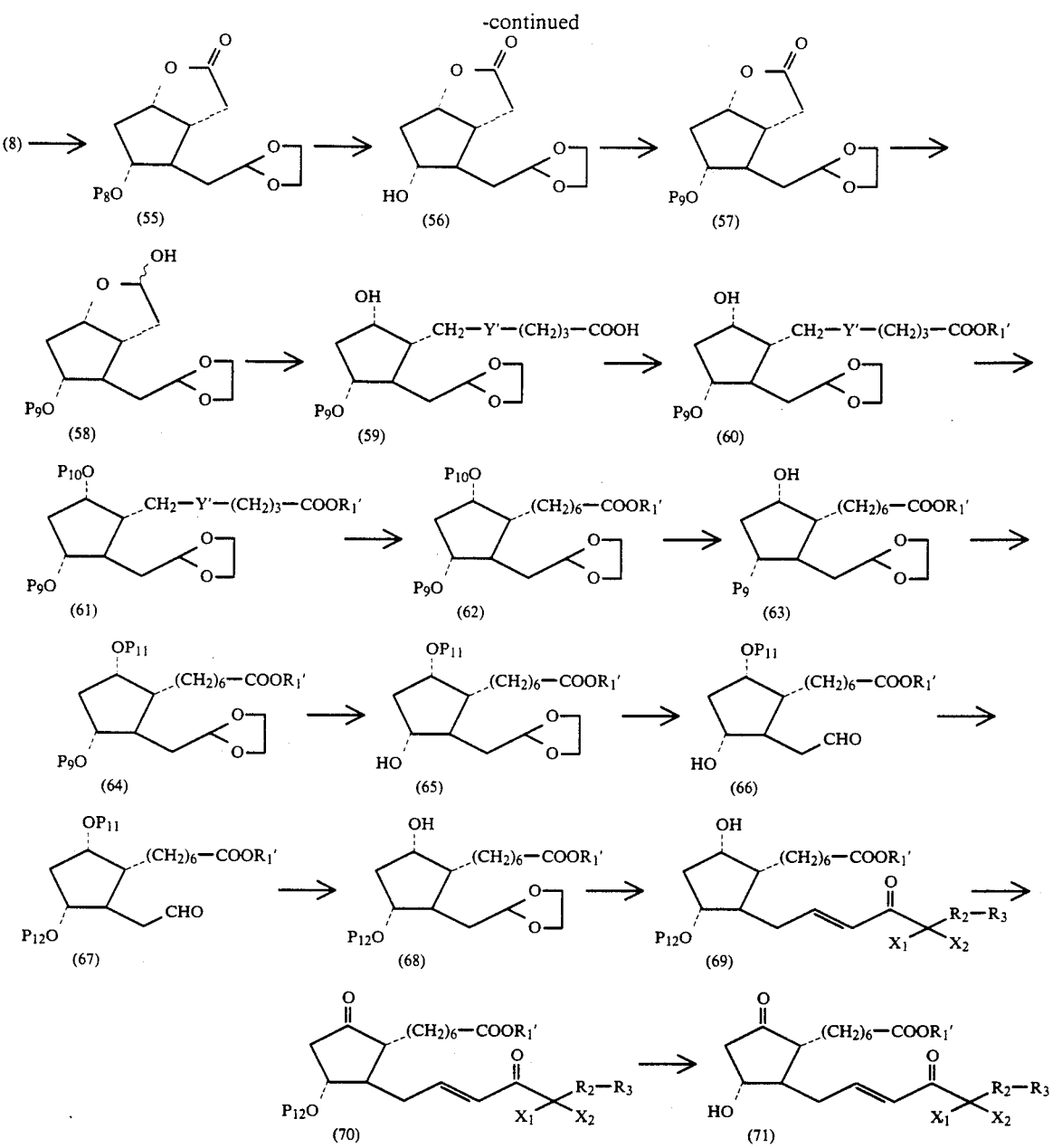

Referring to the above Schemes, the process steps from the compound (1) to the compound (7) show a reaction for elongation of the carbon chain. In the first place, a leaving group (such as tosyl) is introduced to Corey lactone (1) having an appropriate protecting group (for example, 4-phenylbenzoyl) (commercially available) to form the compound (2), which is reacted with a compound generating cyamide ion to give the nitrile (3). Deprotection of it produces the compound (4), the cyano group in which is hydrolyzed to form the compound (5). After introducing a protective group (preferably acyl such as acetyl) to give the compound (6), the carboxy group is reduced to yield the compound (7) that is a compound in which the number of the carbon atoms in the chain is increased by 1.

The compound (7) is oxidized (for example, by Collins oxidation) into the compound (8), which is reacted with (2-oxoalkyl)phosphonate having desired $X_1$, $X_2$, $R_2$ and $R_3$ to yield the compound (9). As the phosphonate, (3,3-difluoro-2-oxoalkyl)phosphonate (when $X_1$ and $X_2$ are fluorine), (3,3-dimethyl-2-oxoalkyl)phosphonate (when $X_1$ and $X_2$ are methyl), (3-fluro, 3-methyl-2-oxoalkyl)phosphonate (when $X_1$ is fluorine and $X_2$ is mehtyl) or (2-oxo-4-phenylbutyl)phosphonate (when $R_2$ is methylene and $R_3$ is phenyl) may be used. If a 14,15- dihydro compound is desired, the compound (9) is subjected to reduction of the double bond to form the compound (10), and of which oxo group is reduced to give the compound (11), of which hydroxy group is protected to give the compound (12). The acyl protecting group for the hydroxy group at position 11 is removed to give the compound (13) and another protecting group (such as tetrahydropyranyl) is introduced to form the compound (14), of which the lactone ring is then reduced to the corresponding lactol (15). To this is introduced an alpha-chain by Witig reaction to produce the compound (16), which is esterified to the compound

(17) and protection group of the hydroxy group at position 16 is removed to give the compound (18). Oxidation of the hydroxy groups at position 16 and 9 giving the compound (19) and deprotection of the hydroxy group at position 11 gives the desired compound (20). In the above preparation, when the reduction of the compound (9) to the compound (10) is omitted, the compound wherein Z is —CH$_2$—CH=CH= is obtained. The compound wherein Z is —CH=CH—CH$_2$- can be obtained from Corey lactone (1) which is oxidized, without the reaction for elongation of the carbon chain, to give the aldehyde (24), which is reacted with a (3-hydroxyalkyl)triaryl- phosphonium halide (B) to give the compound (25). This compound is processed in a manner similar to that for the preparation of the compound (12) to produce the desired compound. This is a mixture of cis- and trans-compounds in respect of the double bond at positions 13 and 14, and can be separated by suitable conventional means. The compound wherein Y is —CH$_2$—CH$_2$— can be obtained by using appropriately selected alpha-chain introducing agent or by reducing the compound (18), followed by oxidation and deprotection, via the dihydro compound (33) and the diketone (34). The compound wherein R$_1$ is a hydrogen atom is obtained after hydrolysis of the compound (20).

In another process, the compound (18) is hydrolyzed to the compound (21), which is oxidized with an oxidizing agent, for example chromic acid, to the compound (22) and then the protecting group of the hydroxy group at position 11 is removed to produce the desired compound (23).

In a further process, in which the compound (I) wherein L is other than a hydroxy group (for example, L is lower alkyl) is desired, the lactone ring of the compound (13) is reduced to form the compound (26), to which the alpha-chain is introduced by Witig reaction to give the compound (27). The hydroxy group at position 11 is protected with, for example, a monocyclic arylsulfonyl group to give the compound (28), which is oxidized (by, for example, Jones oxidation) to be the compound (29). This is reacted with a lower alkyl copper complex to

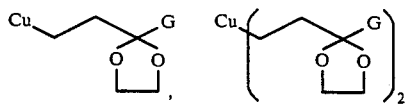

wherein G is alkyl yield the compound (30), of which protection group for the hydroxy group at position 16 is removed. The obtained alcohol (31) is oxidized to produce the desired compound (32).

The PGD-type compounds can be obtained by reducing the compound (13) to the lactol (36), to which the alpha-chain is introduced to form the diol (37). This is converted to the 11-protected compound (38), 9,11-deprotection compound (39), 9-protected compound (40), 16-deprotected compound (41) and then to diketone (42), which at position 9 is removed to produce the compound (43).

The PGA-type compounds can be obtained by oxidation of the 16-deprotected compound (44), which is obtained from the compound (29), to the compound (45).

The PGF-type compounds can be obtained after introduction of a protective group to the compound (27) to give the compound (46), which is deprotected at the side chain to form the compound (47), oxidized to the compound (48) and then deprotected to produce the compound (49). The 6-keto compounds are produced by the reaction with the 5,6-ethylenic compound (50) with N-bromosuccinimide or iodine to form the compound (51), which is treated with DBU (1,8-diazabicyclo-[5.4.0]undec-7-ene). The 5,6-dehydro compounds (i.e. acetylenic compounds) (54) are obtained by the reaction with the copper enolate, generated from the compound (53) and copper complex, with 6-alkoxycarbonyl-1-iodo-2-hexyne.

Further, 14,15-ethylenic compounds (71) can be prepared from compound (8) via compounds (55)-(70). Thus, the aldehyde functionality of the compound (8) is protected by converting it into acetal using ethylene glycol to give the compound (55), which is deprotected to produce the alcohol (56). The alcohol (57) is re-protected with another protective group such as tetrahydropyranyl and then reduced to the lactol (58), to which the alpha-chain is introduced by Witig reaction to give the compound (59). The carboxy group is esterified to produce the compound (60) and the hydroxy group is protected by an easily cleavable protective group such as silyl to give the compound (61). The unsaturation in the alpha-chain is catalytically hydrogenated to form the compound (62), which is deprotected to give the compound (63) and re-protected by another protective group such as acyl to prodece the compound (64). The protected hydroxy at position 3 is deprotected to the compound (65) and then the protected aldehyde is deprotected to the compound (66). The free hydroxy is re-protected to give the compound (67). The protected hydroxy at position 5 is deprotected and aldehyde is protected to produce the compound (68), which is reacted with (2-oxoalkyl)phosphonate having desired X$_1$, X$_2$, R$_2$ and R$_3$ to give the compound (69). This is then oxidized to the compound (70), which is deprotected to the desired compound (71).

Since the compounds (I) have not only improved chemical stability and reduced rate of metabolic degradation but also desired activity or activities out of a wide range of activities of PGs (cf. for example Kirk-Othmer ENCYCLOPEDIA OF CHEMICAL TECHNOLOGY, 3rd. Ed., Supplement Vol., P.721) with less or almost no activity or activities undesirous for human or other animal in the situation in which the compounds are administered, the said compounds are useful as new PG derivatives having selected activity or activities. Such activity or activities can be measured by the conventional pharmacological assay methods which have been used for evaluating the activities of natural and synthetic PGs. In addition, the compounds of the invention are useful as stable reference agents having activities of PGs and usable in comparative biochemical test.

Particularly, the 15-dehydroxy-16-oxo-PG compounds are useful as a platelet aggregation inhibitor.

The compounds of the present invention may be used as a medicine for animals and human beings and usually applied systemically or locally by such methods as oral administration, intravenous injection (including instillation), subcutaneous injection, suppository and the like. While the dosage will vary depending on the particular kind of subject such as animal or human patient, age, body weight, symptom to be treated, desired therapeutic effect, administration route, term of treatment and the like, satisfactory effects will be obtained with the dosage of 0.001–500 mg/kg administered systemically in 2 to 4 divided doses a day or as a sustained form.

As a solid composition of this invention for oral administration, tablets, troches, buccals, capsules, pills, powders, granules and the like are included. The solid composition containing one or more active substances is mixed with at least an inactive diluent, e.g. lactose, cellulose, silicic acid anhydride, etc. The composition may contain additives other than the inactive diluent, for example, lubricants, a disintegrator. Tablets and pills may be coated with an enteric or gastroenteric film, if necessary, and furthermore they may be covered with two or more layers. Additionally, the composition may be in the form of capsules made of substance easily absorbed. The composition may be in the form of buccals, when an immediate effect is desired.

Liquid compositions for oral administration include pharmaceutically acceptable emulsions, solutions, suspension, syrups, elixirs and the like and contain a commonly used inactive diluent e.g. purified water or ethyl alcohol. The composition may contain additives e.g. wetting agents, suspending agents, sweeteners, flavors, perfumes and preservatives.

An injection of this invention for non-oral administration includes sterile aqueous or nonaqueous solutions, suspensions, and emulsions. The composition may contain other additives, e.g. preservatives, wetting agents, emulsifying agents, dispersing agents and the like. These are sterilized by filtration through, e.g. a bacteria-retaining filter, compounding with a sterilizer, gas sterilization or radiation sterilization. These can be prepared by producing a sterilized water or a sterilized solvent for injection before use.

Another formulation according to the present invention is a rectal or vaginal suppository. This can be prepared by mixing at least one active compound according to the invention with a suppository base and optionally containing nonionic surfactant for improving absorption.

EXAMPLE

The practical embodiments for the production of the invention are illustratively shown in the following Examples.

EXAMPLE 1

Preparation of
15-dehydroxy-17,17-difluoro-13,14-dihydro-16-oxo-PGE$_2$ (20) methyl ester [The IUPAC nomenclature:methyl (Z)-7-[(1R)-(2R,3R)-2-(5,5-difluoro-4-oxooctyl))-3-hydroxy-5-oxocyclopentyl]hept-5-enoate]

1-1) Preparation of
(1S,5R,6R,7R)-6-cyanomethyl-7-hydroxy-2-oxabicyclo[3.3.0]octan-3-one (4)

P-toluenesulfonyl chloride (30.3 g) as added to a solution of commercially available (−)-Corey lactone (1) (15.0 g) in pyridine, and the resultant mixture was stirred for 15 hours.

The reaction mixture was worked up with the conventional procedure to give the crude tosylate (2).

The tosylate (2) was dissolved in dimethyl sulfoxide and sodium cyanide (3.92 g) was added thereto, and the resultant mixture was stirred at 60° to 70° C. for 2 hours. The reaction mixture was worked up with the conventional procedure to give the crude cyano compound (3). The crude cyano compound (3) was dissolved in methanol, and potassium carbonate (2.76 g) was added thereto, and the resultant mixture was stirred for 15 hours. The reaction mixture was concentrated under reduced pressure, and the obtained residue was chromatographed on a silicagel column to give the titled compound (4).

Yield: 3.93 g (51%)

1-2) Preparation of 2-{(6R)-(1S,5R,7R)-7-acetoxy-3-oxo-2-oxabicyclo[3.3.0]octyl}-acetic acid (6)

(1S,5R,6R,7R)-6-Cyanomethyl-7-hydroxy-2-oxabicyclo[3.3.0]octan-3-one (4) (1.25 g) was dissolved in 1N sodium hydroxyde solution and the resultant mixture was stirred at 100° to 110° C. The reaction mixture was allowed to be cool, neutralized with hydrochloric acid and concentrated under reduced pressure. To the obtained residue were added ethyl acetate and methanol, and insoluble materials were removed by filtration. The filtrate was concentrated under reduced pressure to give the crude carboxylic acid (5). To the carboxylic acid (5) were added acetic anhydride (20 ml) and pyridine (10 ml), and the resultant mixture was stirred for 15 hours. The reaction mixture was concentrated under reduced pressure and the obtained residue was treated with 1N hydrochloric acid and the resultant mixture was stirred for 1 hour. The reaction mixture was worked up with the conventional procedure to give the crude titled compound (6).

1-3) Preparation of (1S,5R,6R,7R)-7-acetoxy-6-(2-hydroxy-ethyl)-2-oxabicyclo[3.3.0]octan-3-one (7)

The product obtained in 1-2), namely 2-[(6R)-(1S,5R,7R)-7-acetoxy-3-oxo-2-oxabicyclo[3.3.0]octyl]acetic acid (6), was dissolved in ethyl actate and the resultant solution was cooled to 0° C. Boron dimethyl sulfide complex (0.65 ml) was added and the solution was stirred for 3 hours at room temperature. Methanol (6 ml) was added to the reaction mixture and the resultant mixture was concentrated under reduced pressure. The obtained residue was subjected to silicagel column chromatography to give the titled compound (7).

Yield: 0.803 g (51%, calculated from Compound (4))

1-4) Preparation of
(1S,5R,6R,7R)-7-acetoxy-6-[(E)-5,5-difluoro-4-oxo-2-octenyl]-2-oxabicyclo[3.3.0]octan-3-one (9)

A solution of oxalyl chloride (0.90 ml) in methylene chloride was cooled to −78° C. and dimethyl sulfoxide (DMSO) (1.64 ml) was added thereto.

To the resultant mixture was added (1S,5R,6R,7R)-7-acetoxy-6-(2-hydroxyethyl)-2-oxabicyclo[3.3.0]octan-3-one (7) (1.77 g) in methylene chloride. After 30 minutes, the resultant solution was warmed to −30° C. Trimethylamine (3.28 ml) was added and the mixture was stirred for additional 30 minutes. To the reaction mixture was added saturated ammonium chloride solution. The resultant mixture was worked up with the conventional procedure to give the crude aldehyde product (8).

To a solution of thallium(I) ethoxide (1.29 g) in tetrahydrofuran (THF) was added a solution of dimethyl (3,3-difluoro-2-oxohexyl)phosphonate (1.39 g) in THF. The resultant solution was cooled to 0° C., followed by addition of a solution of the aldehyde (8) in THF. The resultant mixture was stirred for 15 hours, and neutralized with acetic acid. An aqueous potassium iodide solution was added and insoluble matters were removed by filtration. The filtrate was worked up with the conventional procedure and the obtained residue was subjected to silicagel column chromatography to give the title compound (9).
yield: 0.967 g (54%)

1-5) Preparation of (1S,5R,6R,7R)-7-acetoxy-6-{78 5,5-difluoro-4-(RS)-hydroxyoctyl}-2-oxabicyclo[3.3.-0]octan-3-one. (11)

Palladium on charcoal (0.200 g) was added to a solution of (1S,5R,6R,7R)-7-acetoxy-6-[(E)-5,5-difluoro-4-oxo-2-octenyl]-2-oxabicyclo[3.3.0]octan-3-one (9) (1.55 g) in ethyl acetate. The resultant mixture was stirred for 15 hours under a hydrogen atmosphere. The reaction mixture was filtered and the filtrate was concentrated under reduced pressure to give the crude ketone (10).

Sodium borohydride (0.169 g) was added to a solution of crude ketone (10) in methanol. After 30 minutes, acetic acid was added and the resultant mixture was worked up with the conventional procedure. The obtained crude product was subjected to silicagel column chromatography to give the titled compound (11)
Yield: 1.52 g (97%)

1-6) Preparation of (1S,5R,6R,7R)-6-{4(RS)-t-butyl dimethylsiloxy-5,5-difluorooctyl}-7-hydroxy-2-oxabicyclo[3.3.0]octan-3-one (13)

Imidazol (1.78 g) and t-butyldimethylsilyl chloride (1.97 g) were added to a solution of (1S,5R,6R,7R)-7-acetoxy-6-{5,5-difluoro-4-(RS)-hydroxyoctyl}-2-oxabicyclo[3.3.0]-octan-3-one (11) (1.52 g) in N,N-dimethyl formamide. The resultant solution was stirred for 3 days.

The reaction mixture was worked up with the conventional procedure to give the crude silyl product (12). The obtained silyl product (12) was dissolved into methanol, followed by addition of potassium carbonate (0.60 g). The resultant mixture was stirred for 2 hours. The reaction mixture was worked up with the conventional procedure and the obtained product was subjected to silicagel column chromatography to give the titled compound (13).
Yield: 1.63 g (89%)

1-7) Preparation of (1S,5R,6R,7R)-6-{4(RS)-t-butyldimethylsiloxy-5,5-difluorooctyl}-7-tetrahydropyranyloxy-2-oxabicyclo[3.3.0]octan-3-one (14)

To a solution of (1S,5R,6R,7R)-6-[4(RS)-t-butyl-dimethyl-siloxy-5,5-difluorooctyl]-7-hydroxy-2-oxabicyclo[3.3.0]octan-3-one (13) (1.63 g) in methylene chloride were added dihydropyran (1.70 ml) and p-toluene sulfonic acid monohydrate (20 mg). After 30 minutes, the resultant mixture was worked up with the conventional procedure and the obtained residue was subjected to silicagel column chromatography to give the titled compound (14).
Yield: 1.93 g (99%)

1-8) Preparation of methyl (Z)-7-[(1R)-(2R,3R,5S)-2-{4(RS)-t-butyldimethyl-siloxy-5,5-difluorooctyl}-5-hydroxy-3-tetrahydropyranyloxycyclopentyl]hept-5-enoate (17)

Diisobutylaluminium hydride (DIBAL-H) (1.0M, 11.5 ml) was added to a solution of (1S,5R,6R,7R)-6-{4(RS)-t-butyl-dimethylsiloxy-5,5-difluorooctyl}-7-tetrahydropyranyloxy-2-oxabicyclo[3.3.0]octan-3-one (14) (1.93 g) in toluene. After 30 minutes, methanol and a saturated Rochelle salt solution were added and the resultant mixture was worked up with the conventional procedure to give the crude lactol (15).

To a suspension of (4-carboxybutyl)-triphenylphosphonium bromide (6.80 g) in THF was added dropwise a solution of potassium t-butoxide (1.0M, 30.7 ml). The resultant mixture was stirred for 15 minutes. The reaction mixture was cooled to $-40°$ C. and a solution of the lactol (15) prepared above in tetrahydrofuran was added thereto. The reaction temperature was kept at 25° C. while stirring for 15 hours and worked up with the conventional procedure to give the crude carboxylic acid (16).

To a solution of the crude carboxylic acid (16) in ether was added a solution of diazomethane in ether prepared with the ordinal method. The reaction mixture was concentrated under reduced pressure, and the obtained residue was subjected to column chromatography with silica gel to give the titled compound (17).
Yield: 1.90 g (82%)

1-9) Preparation of methyl (Z)-7-[(1R)-(2R,3R,5S)-2-{5,5-difluoro-4(R,S)-hydroxyoctyl}-5-hydroxy-3-tetrahydropyranyloxycyclopentyl]hept-5-enoate (18)

To a solution of methyl (Z)-7-[(1R)-(2R,3R,5S)-2-{4(RS)-t-butyldimethylsiloxy-5,5-difluorooctyl}-5-hydroxy-3-tetrahydropyranyloxycyclopentyl]hept-5-enoate (17) (1.90 g) in tetrahydrofuran was added tetrabutylammonium fluoride in tetrahydrofuran (1.0M, 15.7 ml). The resultant mixture was stirred at room temperature for 3 days. The reaction mixture was concentrated under reduced pressure and the obtained residue was subjected to silicagel column chromatography to give the titled compound (18).
Yield: 1.16 g (75%)

1-10) Preparation of methyl (Z)-7-[(1R)-(2R,3R)-2-(5,5-difluoro-4-oxooctyl)-5-oxo-3-tetrahydropyranyloxycyclopentyl]hept-5-enoate (19)

A solution of oxalyl chloride (0.165 ml) in methylene chloride was cooled to $-78°$ C. and dimethyl sulfoxide (DMSO) (0.30 ml) was added thereto.

To the above solution was added a solution of methyl (Z)-7-[(1R)-(2R,3R,5S)-2-{5,5-difluoro-4(RS)-hydroxyoctyl}-5-hydroxy-3-tetra-hydropyranyloxycyclopentyl]hept-5-enoate (18) (0.244 g) in methylene chloride. The resultant mixture was warmed to $-25°$ C. and stirred for 1 hour. Triethylamine (0.60 ml) was added thereto and the reaction mixture was stirred for additional 30 minutes, poured into 1N hydrochloric acid, and then worked up with the conventional procedure. The obtained product was subjected to silicagel column chromatography to give the titled compound (19).
Yield: 0.20 g (83%)

1-11) Preparation of 15-dehydroxy-17,17-difluoro-13,14-dihydro-16-oxo-PEG$_2$ methyl ester [methyl (Z)-7-{(1R)-(2R,3R)-2-(5,5-difluoro-4-oxooctyl)-5-oxo-3-hydroxycyclopentyl}hept-5-enoate (20)]

Methyl (Z)-7-[(1R)-(2R,3R)-2-{5,5-difluoro-4-oxooctyl}-5-oxo-3-tetrahydropyranyloxycyclopentyl]hept-5-enoate (19) (0.20 g) was dissolved in a mixed solvent of acetic acid, water and tetrahydrofuran (4:2:1) and the resultant solution was stirred at 45° to 50° C. for 3 hours. The reaction mixture was concentrated under reduced pressure and the obtained product was subjected to silicagel column chromatography and further to medium pressure chromatography on Rober column (Merck & Co.,Inc. ODS, type B) to give the titled compound (20).

Yield: 0.124 g (75%)

Compound (20) ($X_1=X_2=F$, $R_2$-$R_3$=propyl, $R'_1$=methyl)

$^1$HNMR (CDCl$_3$) δ 0.98(t,3H,J=7Hz),1.1–2.80 (m,22H),3.11(m,1H),3.68(s,3H),4.12–4.27(m,0.73H),4.32–4.47 (m,0.27H),5.25–5.54(m,2H)

MS (DI-EI)m/z402(M+),384(M+-H$_2$O),368(M+-HF-H$_2$O),353(M+ -OCH$_3$-H$_2$O),309(M+-C$_4$H$_7$F$_2$)

EXAMPLE 2

Preparation of 15-dehydroxy-17,17,-difluoro-13,14-dihydro-16-oxo-PGE$_2$ (23) [The IUPAC nomenclature:(Z)-7-{(1R)-(2R,3R)-2-(5,5-difluoro-4-oxooctyl)-5-oxo-3-hydroxycyclopentyl}hept-5-enoic acid]

2-1) Preparation of (Z)-7-{(1R)-(2R,3R)-2-(5,5-difluoro-4-oxooctyl)-5-oxo-3-tetrahydropyranyloxycyclopentyl}hept-5-enoic acid (22)

1N Sodium hydroxide solution (4.8 ml) was added to a solution of methyl (Z)-7-[(1R)-(2R,3R,5S)-2-{5,5-difluoro-4(RS)-hydroxyoctyl}-5-hydroxy-3-tetrahydropyranyloxycyclopentyl]hept-5-enoate (18) (0.457 g) in methanol. The resultant mixture was stirred for 4 hours and treated in the conventional manner to give dialcohol (21).

Chromic acid (3.67 g) was added to pyridine (5.93 ml) in methylene chloride. The resultant mixture was stirred for 1 hour and celite was added thereto. A solution of the diol (21) in methylene chloride was added and the resultant mixture was stirred for 30 minutes. Then, sodium bisulfate (30 g) was added thereto. The reaction mixture was worked up with the conventional procedure to give a crude product, which was subjected to procedure silicagel (Mallincklodt, CC-4) column chromatography to give the titled compound (22).

Yield: 0.231 g (53%)

2-2) Preparation of 15-dehydroxy-17,17-difluoro-13,14-dihydro-16-oxo-PGE$_2$ (23) [The IUPAC nomenclature: (Z)-7-{(1R)-(2R,3R)-2-(5,5-difluoro-4-oxooctyl)-5-oxo-3-hydroxycyclopentyl}hept-5-enoic acid]

A solution of (Z)-7-[(1R)-(2R,3R)-2-(5,5-difluoro-4-oxooctyl)-5-oxo-3-tetrahydropyranyloxycyclopentyl]-hept5-enoic acid (22) (0.231 g) in a mixed solvent of acetic acid, water and tetrahydrofuran (4:2:1) was stirred at 45° C. for 3.5 hours. The reaction mixture was concentrated under reduced pressure and the obtained residue was subjected to medium pressure chromatography on a Rober column (Merck, & Co., Inc., ODS, type B) to give the titled compound (23).

Yield: 0.110 g (58%)

Compound (23) ($X_1=X_2=F$, $R_2$-$R_3$=propyl)

$^1$HNMR (CDCl$_3$) δ 1.00(t,3H,J=7Hz),1.10–2.80(m,22H),4.12–4.27 (m,0.71H),4.32–4.46(m,0.29H),5.27–5.55(m,2H),4.0–6.5 (br.s,2H).

MS (DI-EI)m/z388(M+),370(M+-H$_2$O).

EXAMPLE 3

Preparation of 15-dehydroxy-17,17-difluoro-13,14-dihydro-16-oxo-PGE$_2$ isopropyl ester (20) [The IUPAC nomenclature: Isopropyl (Z)-7-{(1R)-(2R,3R)-2-(5,5-difluoro-4-oxooctyl)-3-hydroxy-5-oxocyclopentyl} hept-5-enoate]

3-1) Preparation of Isopropyl (Z)-7-[(1R)-(2R,3R,5S)-2-{4(R,S)-t-butyldimethylsiloxy-5,5-difluorooctyl}-5-hydroxy-3-tetrahydropyranyloxycylopentyl]hept-5-enoate (17)

To a solution of the crude carboxylic acid (16) in acetonitrile were added isopropyl iodide (0.85 ml) and 1,8-diazabicyclo[5.4.0]undec-7-ene (DBU) (1.29 ml). The resultant mixture was kept at 60° to 65° C. for 2 hours. The crude product obtained after the usual work-up was subjected to silicagel column chromatography, to give the titled compound (17).

Yield: 1.1 g (87%)

3-2) Preparation of isopropyl (Z)-7-[(1R)-(2R,3R,5S)-2-{4(R,S)-hydroxy-5,5-difluorooctyl}-5-hydroxy-3-tetrahydropyranyloxycylopentyl]hept-5-enoate (18)

To a solution of the compound (17) (1.1 g) in THF was added tetrabutylammonium fluoride (1M THF, 5.5 ml). The resultant mixture was stirred for 1 hour and 20 minutes. The product obtained after the usual work-up was subjected to silicagel column chromatography to give the titled compound (18).

Yield: 0.906 g (100%)

3-3) Preparation of isopropyl (Z)-7-{(1R)-(2R,3R,5S)-2-(5,5-difluoro-4-oxooctyl)-5-oxo-3-tetrahydropyranyloxycylopentyl}hept-5-enoate (19)

A solution of oxalyl chloride in methylene chloride (2M, 3.5 ml) was cooled to −78° C., followed by addition of DMSO (1.1 ml). A solution of the compound (18) (0.906 g) in methylene chloride (11 ml) was added dropwise. The resultant mixture was stirred at the range of −35° to −25° C. for 1.5 hours, and triethylamine (2.1 ml) was added dropwise. After 20 minutes, 1N hydrochloric acid was added. The crude product obtained after the usual work-up was subjected to silicagel column chromatography to give the titled compound (19).

Yield: 0.785 g (87.7%)

3-4) Preparation of isopropyl (Z)-7-{(1R)-(2R,3R)-2-(5,5-difluoro-4-oxooctyl)-5-oxo-3-hydroxycylopentyl}-hept-5-enoate (20)

A solution of the compound (19) (0.785 g) in a mixed solvent of acetic aid, THF and water (3:1:1, 70 ml) was kept at 50° C. for 4.5 hours. The crude product obtained after the usual work-up was subjected to silicagel column chromatography to give the titled compound (20).

Yield: 0.335 g

Compound (20) ($X_1=X_2=F$, $R_2$-$R_3$=propyl, $R'_1$=methyl) $^1$HNMR (CDCl$_3$) δ 0.94(t,3H,J=7.4Hz),1.20(d,6H,J=6.2Hz), 1.3–2.9(m,22H),4.17(m,1H),4.98(hept,1H,J=62Hz),5.22–5.52 (m,2H).

MS (DI-ZI) m/z 430(M+),412(M+-H$_2$O),371(M+-C$_3$H$_7$O), 353(M+-C$_3$H$_7$O-H$_2$O)

EXAMPLE 4

Preparation of 11,15-didehydroxy-17,17-difluoro-13,14-dihydro-11-methyl-16-oxo-PGE$_2$ methyl ester (32) [The IUPAC nomenclature: methyl (Z)-7-{(1R,2S,3R)-2-(5,5-difluoro-4-oxooctyl)-3-methyl-5-oxocylopentyl}hept-5-enoate]

4-1) Preparation of {1S,3(R,S),5R,6R,7R}-6-{4(R,S)-t-butyldimethylsiloxyoctyl-5,5-difluorooctyl}-3,7-dihydroxy-2-oxabicyclo[3.3.0]octane (26)

A solution of (1S,5R,6R,7R)-6-{4(R,S)-t-butyldimethylsiloxy-5,5-difluorooctyl}-7-hydroxy-2-oxabicyclo[3.3.0]octan-3-one (13) (1.06 g) in toluene was cooled to −78° C. and DIBAL-H (1.5M, 7.56 ml) was added dropwise thereto. After 30 minutes methanol (8 ml) was added. The reaction mixture was worked up with the conventional manner to give the lactol (26).

4-2) Preparation of methyl (Z)-7-[(1R)-(2R,3R,5S)-2-{(4(R,S)-t-butyldimethylsiloxy-5,5-difluorooctyl}-3,5-dihydroxycylopentyl]-hept-5-enoate (27)

To a suspension of (4-carboxybutyl)triphenylphosphonium bromide (6.7 g) in THF (5 ml) was added dropwise potassium t-butoxide (1.0M, in THF solution) (30.2 ml). The resultant mixture was stirred at room temperature for 30 minutes, and then cooled to −40° C. A solution of lactol (26) in THF (15 ml) was added thereto. The resultant mixture was stirred overnight at −20° C. The crude carboxylic acid obtained after the usual work-up was esterified with diazomethane. The obtained product was subjected to silicagel column chromatography to give the diol (27).

Yield: 1.12 g (85%)

4-3) Preparation of methyl (Z)-7-[(1R)-(2R,3R,5S)-2-{(4(R,S)-t-butyldimethylsiloxy-5,5-difluorooctyl}-5-hydroxy-3-(p-toluenesulfoxy)cylopentyl]hept-5-enoate (28)

A solution of the diol (27) (0.574 g) in pyridine was cooled to −20° C., followed by addition of p-toluenesulfonyl chloride (2.1 g). The resultant mixture was stirred for 1 hour at −20° C. and for additional 2 hours at 0° C. The crude product obtained after the usual work-up was subjected to silicagel column chromatography to give the monotosylate (28).

Yield: 0.465 g (63%)

4-4) Preparation of methyl (Z)-7-[(1R,2R)-2-{4(R,S)-t-butyldimethylsiloxy-5,5-difluorooctyl}-5-oxocylopent-3-enyl]hept-5-enoate (31)

A solution of the monotosylate (15) (0.465 g) in acetone (20 ml) was cooled to −30° C. and Jones reagent (0.9 ml) was added dropwise thereto. The resultant mixture was stirred at the range of −20° to 10° C. for 50 minutes, followed by addition of isopropanol (0.9 ml). After stirring for 20 minutes, the reaction mixture was worked up with the conventional procedure. The obtained crude product was subjected to silicagel column chromatography to give the α,β-unsaturated ketone (29).

Yield: 0.201 g (71%)

4-5) Preparation of methyl (Z)-7-[(1R,2S,3R)-2{4(R,S)-t-butyldimethylsiloxy-5,5-difluorooctyl}-3-methyl-5-oxocylopentyl]hept-5-enoate (30)

Copper (II) iodide (0.313 g) was added to anhydrous ether (15 ml). The resultant suspension was cooled to 0° C. and methyl lithium (1.4M, 2.35 ml) was added thereto. After the resultant mixture became colorless and clear, a solution of the α,β-unsaturated ketone (29) in ether (15 ml) was added thereto. The crude product obtained after the usual work-up was subjected to silicagel column chromatography to give the titled compound (30).

Yield: 0.201 g (71%)

4-6) Preparation of methyl (Z)-7-[(1R,2S,3R)-2{4(R,S)-hydroxy-5,5-difluorooctyl}-3-methyl-5-oxocylopentyl]-hept-5-enoate (31)

Hydrofluoric acid (1 ml) was added to a solution of the compound (30) (0.201 g) in acetonitrile (20 ml). The resultant mixture was stirred at room temperature for 1 hour. The crude product obtained after the usual work-up was subjected to silicagel column chromatography to give the alcohol (31).

Yield: 0.138 g (88%)

4-7) Preparation of methyl (Z)-7-[(1R,2S,3R)-2-(5,5-difluoro-4-oxooctyl)-3-methyl-5-oxocylopentyl]hept-5-enoate (32)

Celite (5 g) was added to Collins reagent prepared from chromic anhydride (1.2 g) and pyridine in methylene chloride (20 ml), followed by addition of a solution of the alcohol (31) (0.138 g) in methylene chloride (10 ml). The resultant mixture was stirred at room temperature for 30 minutes, followed by the usual work-up. The obtained crude product was subjected to silicagel column chromatography to give the titled compound (32).

Yield: 81%

Compound (32) (L′=methyl, $X_1=X_2=F$, $R_2$-$R_3$=propyl, $R'_1$=methyl)

$^1$HNMR (CDCl$_3$) δ 0.97(t,3H,J=7.5Hz),1.13(d,3H,J=6Hz), 1.35–2.80(m,23H),3.67(s,3H),5.23–5.50(m,2H).

MS (DI-ZI) m/z 400(M+),369(M+-CH$_3$O)

EXAMPLE 5

Preparation of 15-dehydroxy-17,17-difluoro-13,14-dihydro-16-oxo-PGE$_1$ methyl ester (32) [The IUPAC nomenclature: methyl 7-{(1R)-(2R,3S)-2-(5,5-difluoro-4-oxooctyl)-3-hydroxy-5-oxocylopentyl}hept-5-enoate]

5-1) Preparation of 7-[(1R)-(2R,3S,5S)-2-{5,5-difluoro-4(R,S)-hydroxyoctyl}-5-hydroxy-3-tetrahydropyranyloxycylopentyl]-heptanoate (33)

Palladium on carbon (Pd-C) (100 mg) was added to a solution of the diol (18) (0.465 g) in ethyl acetate (30 ml). The resultant mixture was stirred overnight under a hydrogen atmosphere. The reaction mixture was filtered and the filtrate was concentrated under reduced pressure to give the dihydro compound (33).

Yield: 0.450 g (98%)

5-2) Preparation of methyl 7-{(1R)-(2R,3R)-2-(5,5-difluoro-4oxooctyl)-5-oxo-3-tetrahydropyranyloxycylopentyl}heptanoate (34)

Celite (10 g) was added to Collins reagent prepared from chromic anhydride (3.67 g) in methylene chloride (20 ml), followed by addition of the dihydro compound (33) (0.450 g) to be oxidized. The crude product obtained after the usual work-up was subjected to silicagel column chromatography to give the diketone (34).

Yield: 0.371 g (83%)

5-3) Preparation of methyl 7-{(1R)-(2R,3R)-2-(5,5-difluoro-4-oxooctyl)-3-hydroxy-5-oxocylopentyl}heptanoate (35)

The diketone (34) (0.371 g) was dissolved in a mixed solvent of acetic acid, THF and water (1:3:1, 35 ml), and the resultant solution was stirred overnight. The crude product obtained after the usual work-up was chromatographed on a Rober column (ODS) to give the titled compound (35).

Compound (35) ($X_1=X_2=F$, $R_2-R_3=$ propyl, $R'_1=$ methyl)

$^1$HNMR (CDCl$_3$) δ 0.98(t,3H,J=7.5Hz),1.11–2.9(m,26H), 3.67(s,3H),4.1–4.25(m,1H).

MS (DI-ZI) m/z 404(M+),386(M+-H$_2$O),355(M+-H$_2$O-CH$_3$O)

EXAMPLE 6

Preparation of 15-dehydroxy-17,17-difluoro-13,14-dihydro-16-oxo-PGD$_2$ methyl ester (43) [The IUPAC nomenclature: methyl (Z)-7-{(1R)-(2R,5S)-2-(5,5-difluoro-4-oxooctyl)-5-hydroxy-3-oxocylopentyl}hept-5-enoate]

6-1) Preparation of methyl (Z)-7-[(1R)-(2R,3R,5S)-2-{4(R,S)-t-butyldimethylsiloxy-5,5-difluorooctyl}-3,5-dihydroxycylopentyl]heptanoate (37)

The lactone (13) (1.06 g) in toluene cooled to −8° C. was reduced with DIBAL-H (1.5M in toluene, 7.56 ml). The reaction mixture was worked up with the conventional procedure to give the lactol (36). Pottasium butoxide (1.0M in THF, 30.2 ml) was added to a suspension of (4-carboxybutyl)triphenylphosphonium bromide (6.7 g) in THF and the resultant mixture was stirred at room temperature for 30 minutes, and then cooled to −40° C. A solution of the lactol (36) in THF (15 ml) was added thereto, and the mixture was stirred overnight at −20° C. The crude carboxylic acid obtained after the usual work up was esterified with diazomethane and the reaction mixture was subjected to silicagel column chromatography to give the diol (37).

Yield: 1.12 g (85%)

6-2) Preparation of methyl (Z)-7-[(1R)-(2R,3R,5S)-2-{4(R,S)-t-butyldimethylsiloxy-5,5-difluorooctyl}-3-bezoyloxy-5-hydroxycylopentyl]hept-5-enoate (38)

A solution of the diol (37) (0.564 g) and pyridine (0.85 ml) in methylene chloride was cooled to −30° C. Benzoyl chloride (0.147 g) was added thereto and the mixture was stirred for 1 hour. An additional amount (0.440 g) of benzoyl chloride was added to the reaction mixture and the mixture was stirred at −20° C. for 2 hours. The crude product obtained after the usual work-up was subjected to silicagel chromatography to give the compound (38).

Yield: 0.567 g (77%)

6-3) Preparation of methyl (Z)-7-[(1R)-(2R,3R,5S)-2-{4(R,S)-t-butyldimethylsiloxy-5,5-difluorooctyl}-3-bezoyloxy-5-tetrahydropyranyloxycylopentyl-]hept-5-enoate (39)

Dyhydropyran (0.6 ml) was added to a solution of monobezoate compound (38) (0.567 g) in methylene chloride and the resultant mixture was cooled to 0° C. A catalytic amount of p-toluenesulfonic acid was added thereto and the mixture was stirred for 30 minutes. The crude product obtained after the usual work-up was subjected to silicagel column chromatography to give the titled compound (39).

Yield: 0.689 g

6-4) Preparation of methyl (Z)-7-[(1R)-(2R,3R,5S)-2-{4(R,S)-t-butyldimethylsiloxy-5,5-difluorooctyl}-3-hydroxy-5-tetrahydropyranyloxycylopentyl]hept-5-enoate (40)

Potassium carbonate (0.125 g) was added to a solution of the compound (39) (0.689 g) in methanol, and the resultant mixture was stirred at room temperature for 2 hours. An additional amount (1.75 g) of potassium carbonate was added thereto, and the mixture was left on standing overnight. The crude product obtained after the usual work-up was subjected to silicagel column chromatography to give the monoalcohol (40).

Yield: 0.479 g (87%, started from the compound (38))

6-5) Preparation of methyl (Z)-7-[(1R)-(2R,3R,5S)-2-{4(R,S)-hydroxy-5,5-difluorooctyl}-3-hydroxy-5-tetrahydropyranyloxycylopentyl]hept-5-enoate (41)

Tetrabutylammonium fluoride (1.0M in THF, 3.95 ml) was added to a solution of the monoalcohol (40) (0.479 g) in THF and the mixture was stirred overnight at room temperature. The crude product obtained after the usual work-up was subjected to silicagel column chromatography to give the diol (41).

Yield: 72%

6-6) Preparation of methyl (Z)-7-{(1R)-(2R,5S)-2-(5,5-difluoro-4oxooctyl)-3-oxo-5-tetrahydropyranyloxycylopentyl}hept-5-enoate (42)

A solution of oxalyl chloride (0.24 ml) in methylene chloride was cooled to −78° C., followed by addition of DMSO (0.44 ml). After 15 minutes, a solution of the diol (41) (0.358 g) in methylene chloride was added dropwise to the resultant mixture. After 30 minutes, the mixture was warmed to −50° C., followed by stirring for 1.5 hours. Then, the reaction mixture was allowed to warm to −35° C. and triethylamine (0.88 ml) was added thereto. The crude product obtained after the usual work-up was subjected to silicagel column chromatography to give the diketone (42).

Yield: 0.188 g (53%)

6-7) Preparation of methyl (Z)-7-{(1R)-(2R,5S)-2-(5,5-difluoro-4oxooctyl)-5-hydroxy-3-oxocylopentyl}hept-5-enoate (43)

The diketone (42) (0.188 g) was dissolved in a mixed solvent of acetic acid, THF and water (3:1:1, 25 ml) and the resultant mixture was kept at 40° C. for 3.5 hours. The crude product obtained after the usual work-up was subjected to silicagel column chromatography to give the titled compound (43).

Yield: 0.112 g (72%)

Compound (43) ($X_1=X_2=F$, $R_2$-$R_3$=propyl, $R'_1$=methyl)

$^1$HNMR (CDCl$_3$) δ 0.98(t,3H,J=7.5Hz),1.4–2.8(m,22H), 3.69(s,3H),4.1–4.5(m,1H),5.4–5.6(m,2H).

MS (DI-ZI) m/z 402(M$^+$),384(M$^+$-H$_2$O),353(M$^+$-H$_2$O-CH$_3$O) 333(M$^+$-H$_2$O-CH$_3$O-HF)

EXAMPLE 7

Preparation of 15-dehydroxy-17,17-difluoro-13,14-dihydro-16-oxo-PGA$_2$ methyl ester (45) [The IUPAC nomenclature: methyl (Z)-7-{(1R,2R)-2-(5,5-difluoro-4-oxooctyl)-5-oxocylopent-5-enyl}hept-5-enoate]

7-1) Preparation of methyl (Z)-7-[(1R,2R)-2-{5,5-difluoro-4-(R,S)-hydroxyoctyl}-5-oxocyclopent-3-enyl]hept-5-enoate (44)

The α,β-unsaturated ketone (29) (0.276 g) was dissolved in a solution of aqueous hydrogen fluoride in acetonitrile (46% aqueous hydrogen fluoride:acetonitrile=95:) (20 ml), and the resultant mixture was stirred at room temperature for 2 hours. The crude product obtained after the usual work-up was subjected to silicagel column chromatography to give the alcohol (44).

Yield: 0.180 g

7-2) Preparation of methyl (Z)-7-[(1R,2R)-2-{5,5-difluoro-4-oxooctyl}-5-oxocyclopent-3-enyl]hept-5-enoate (45)

Oxalyl chloride (2M in CH$_2$Cl$_2$) (0.47 ml) was dissolved in methylene chloride (12 ml), followed by addition of DMSO (0.12 ml). The resultant mixture was cooled to −78° C. and a solution of alcohol (44) (0.180 g) in methylene chloride (10 ml) was added. The mixture was stirred at −50° C. for 1 hour. Then, triethylamine (0.23 ml) was added thereto, and the resultant mixture was stirred at −30° C. for 30 minutes.

The crude product obtained after the usual work-up was subjected to silicagel column chromatography to give the titled compound (45).

Yield: 0.126 g (71%)

Compound (45) ($X_1=X_2=F$, $R_2$-$R_3$=propyl, $R'_1$=methyl)

$^1$HNMR (CDCl$_3$) δ 1.00(t,3H,J=7.5Hz),1.40–2.80(m,20H), 3.70(s,3H),5.28–5.55(m,2H),6.17(dd,1H,J=7.5,J=2.),7.-63(dd, 1H,J=7.5,J=2.5).

MS (DI-ZI) m/z 384(M$^+$),353(M$^+$-CH$_3$O)

EXAMPLE 8

Preparation of 15-dehydroxy-17,17-difluoro-13,14-dihydro-16-oxo-PGF$_2$α methyl ester (49) [The IUPAC nomenclature: methyl (Z)-7-{(1R)-(2R,3R,5S)-2-(5,5-difluoro-4-oxooctyl)-3,5-dihydroxycylopentyl}hept-5-enoate]

8-1) Preparation of methyl (Z)-7-[(1R)-(2R,3R,5S)-2-{4(R,S)-t-butyldimethylsiloxy-5,5-difluorooctyl}-3,5-ditetrahydropyranyloxy)-cylopentyl]hept-5-enoate (46)

A solution of methyl (Z)-7-[(1R)-(2R,3R,5S)-2-{4(R,S)-t-butyldimethylsiloxy-5,5-difluorooctyl}-3,5-dihydroxy-cylopentyl]-hept-5-enoate (27) (0.647 g) in dichloromethane (10 ml) was cooled to −5° C., followed by addition of dihydropyran (0.91 ml) and a catalytic amount of p-toluenesulfonic acid. The reaction mixture was gradually warmed to room temperature and kept for 16 hours at the same temperature. The crude product obtained after the usual work-up was subjected to silicagel column chromatography to give the titled compound (46).

Yield: 0.893 g (100%)

8-2) Preparation of methyl (Z)-7-[(1R)-(2R,3R,5S)-2-{5,5-difluoro-4(R,S)-hydroxyooctyl}-3,5-di(tetrahydropyranyloxy)cyclopentyl]-hept-5-enoate (47)

Tetrabutylammonium fluoride (1M in THF, 3.72 ml) was added to a solution of the compound (46) (0.89 g) in THF (12 ml) and the resultant mixture was stirred for 1 hour. The crude product obtained after the usual work-up was subjected to silicagel column chromatography to give the titled compound.

Yield: 0.676 g (95%)

8-3) Preparation of methyl (Z)-7-[(1R)-(2R,3R,5S)-2-{5,5-difluoro-4-oxooctyl}-3,5-di(tetrahydropyranyloxy)cylopentyl]hept-5-enoate (48)

The compound (47) (0.43 ml) was oxidized by Swarn oxidation using 2M oxalyl chloride (0.76 ml), DMSO (0.22 ml) and triethylamine (0.43 ml) in dichloromethane (9 ml). The crude product obtained after the usual work-up was subjected to silicagel column chromatography to give the titled compound (48).

Yield: 0.558 g (82%)

8-4) Preparation of methyl (Z)-7-[(1R)-(2R,3R,5S)-2-{5,5-difluoro-4-oxooctyl}-3,5-di(tetrahydropyranyloxy)cylopentyl]hept-5-enoate (49)

The compound (48) (0.558 g) was dissolved in a mixed solvent of acetic acid, water and THF (4:2:1, 49 ml), and the resultant solution was kept at 45° to 50° C. for 2.5 hours. The crude product obtained after the usual work-up was chromatographed on a silicagel column to give the titled compound (49).

Yield: 0.367 g (94%)

Compound (49) ($X_1=X_2=F$, $R_2$-$R_3$=propyl, $R'_1$=methyl)

$^1$HNMR (CDCl$_3$) δ 0.95(t,3H),1.1–3.0(m,24H),3.66(s,3H), 3.95(s,1H),4.14(s,1H),5.28–5.52(m,2H).

MS (DI-ZI) m/z 404(M$^+$),386(H$^+$-H$_2$ 1.O),368(H$^+$-2H$_2$O)

EXAMPLE 9

Preparation of 15-dehydroxy-17,17-difluoro-13,14-dihydro-20-methyl-16-oxo-PGE$_2$ methyl ester (20) [The IUPAC nomenclature: methyl (Z)-7-{(1R)-(2R,3R)-2-(5,5-difluoro-4-oxononyl)-5-oxo-3-hydroxycylopentyl}hept-5-enoate]

The titled compound (20) was prepared from the compound (8) and dimethyl (3,3-difluoro-2-oxoheptyl)-phosphonate according to the procedure described for the preparation of 15-dehydroxy-17,17-difluoro-13,14-dihydro-20-methyl-16-oxo-PGE$_2$ methyl ester.

Compound (20) ($X_1=X_2=F$, $R_2$-$R_3$=butyl, $R'_1$=methyl)

¹HNMR (CDCl₃) δ 0.94(t,3H),1.1–2.9(m,27H), 3.68(s,3H),4.2(br.s,½H),4.4(q,½H),5.4(m,2H).
MS (DI-ZI) m/z 384(M+-H₂O),353(M+-H₂O-CH₃O)

EXAMPLE 10

Preparation of 15-dehydroxy-17,17-difluoro-13,14-dihydro-16-oxo-PGE₁ isopropyl ester (35) [The IUPAC nomenclature: isopropyl 7-{(1R)-(2R,3R)-2-(5,5-difluoro-4-oxooctyl)-3-hydroxy-5-oxocylopentyl}hept-5-enoate]

A solution of 15-dehydroxy-17,17-difluoro-13,14-dihydro-16-oxo-PGE₂ isopropyl ester (20) (0.303 g) obtained in Example 3 in ethyl acetate (20 ml) was subjected to hydrogenation with a catalytic amount of 5% Pd-C and hydrogen gas. The reaction mixture was filtered and the filtrate was concentrated to give the crude product, which was chromatographed on a Rober column to give the titled compound (35).
Yield: 0.223 g (73%)
Compound (35) ($X_1 = X_2 = F$, $R_2$-$R_3$=propyl, $R'_1$=isopropyl)
¹HNMR (CDCl₃) δ 0.98(t,3H,J=7.5Hz),1.21(d,6H,J=5.5Hz), 1.24–2.82(m,27H),4.1–4.5(m,1H),4.99–(Hept,1H,J=7.5Hz).

EXAMPLE 11

Preparation of 15-dehydroxy-17,17-difluoro-13,14-dihydro-16-oxo-PGE₂ benzyl ester (20) [The IUPAC nomenclature: benzyl (Z)-7-{(1R)-(2R,3R)-2-(5,5-difluoro-4-oxooctyl)-3-hydroxy-5-oxocylopentyl}hept-5-enoate]

The titled compound (20) was prepared as described in Example 3 except that the crude carboxylic acid (16) in acetonitrile was converted to benzyl ester using benzyl bromide and DBU.
Compound (20) ($X_1 = X_2 = F$, $R_2$-$R_3$=propyl, $R'_1$=benzyl)
¹HNMR (CDCl₃) δ 0.96(d,t,3H,J=7.5Hz,J=7.5Hz), 1.1–2.8(m,23H),4.18(m,0.7H),4.36(m,0.3H),5.11(s,2H), 5.38(m,2H),7.35(s,5H).

EXAMPLE 12

Preparation of 15-dehydroxy-17,17-difluoro-13,14-dihydro-16-oxo-PGE₁ [The IUPAC nomenclature: 7-{(1R)-(2R,3R)-2-(5,5-difluoro-4-oxooctyl)-3-hydroxy-5-oxocylopentyl}heptanoic acid]

The benzyl ester (20) (0.580 g) obtained in Example 11 was subjected to catalytic hydrogenation in ethanol (20 ml) using 5% Pd-C (a catalytic amount) and hydrogen gas. The obtained crude product was purified with HPLC (OD column) to give the titled compound.
Yield: 0.426 g (90%)
¹HNMR (CDCl₃) δ 0.98(t,3H,7.5Hz),1.1–2.82(m,28H), 4.07–4.45(m,1H).

The compound having Formula (I) wherein Y is —CO—CH₂— or Y is —C≡C— can be prepared as follows.

EXAMPLE 13

Preparation of
15-dehydroxy-13,14-dihydro-6,16-dioxoPGF₁α isopropyl ester (52)

To a solution of 15-dehydroxy-13,14-dihydro-16,16-ethylenedioxy-11-tetrahydropyranyloxy-PGF₂α (50) in a mixed solvent of tetrahydrofuran and methylene chloride was added N-bromosuccinimide equimolar to the compound (50). The resultant mixture was stirred for 5 minutes. The crude product obtained after the usual work-up was chromatographed on a silicagel column to give the compound (51) ($X_1 = X_2 = H$, $R_2$-$R_3$=propyl, $P_4$=tetrahydropyranyl, $P_7$=ethylene, $R'_1$=isopropyl). DBU was added to a solution of the compound (50) in toluene, and the resultant mixture was stirred overnight at 40° C. After cooling with ice, the reaction mixture was acidified with 1N hydrochloric acid. After stirring for 10 minutes, the solution was extracted with ethyl acetate. The crude product obtained after the usual work-up was chromatographed on a silicagel column to give the titled compound (52) (the symbols have the same meanings as above).

EXAMPLE 14

Preparation of 15-dehydroxy-5,6-dehydro-13,14-dihydro-16-oxo-PGE₂ methyl ester t-Butyllithium was added dropwise over 30 minutes to a solution of 4,4-ethylenedioxyoctane iodide in ether at −78° C., and the resultant mixture was stirred for 3 hours. A solution of copper(I) iodide and tributylphosphine in ether, previously cooled at −78° C., was added in one portion. The reaction mixture was stirred for 20 minutes to produce a complex (a). Further, a solution of 4R-t-butyldimethylsilyloxy-2-cyclopenten-1-one (53) in tetrahydrofuran was added dropwise thereto over 95 minutes, and stirring was continued for 15 minutes. The resultant mixture was transferred in a cooling bath at −30° C. A solution of 8-methoxycarbonyl-2-hexynyl-1-iodide (b) in HMPA was added thereto, and the resultant mixture was stirred at same temperature for 4.5 hours, followed by stirring for additional 12 hours at room temperature. The reaction mixture was poured into saturated aqueous ammonium chloride solution and the organic phase was separated. The crude product obtained after the usual work-up was chromatographed to give the compound (54) ($X_1 = X_2 = H$, $R_2$-$R_3$=propyl, $P_6$=t-butyldimethylsilyl, $P^7$=ethylene, $R'_1$=isopropyl), which was deblocked in the usual work-up to give the titled compound.

EXAMPLE 15

Preparation of
15-dehydroxy-17,17-difluoro-13,14-dihydro-14,15-dehydro-16-oxo-PGE1 methyl ester (71)

15-1) Preparation of
(1S,5R,6R,7R)-7-acetoxy-6-(2,2-ethylenedioxyethyl)-2-oxabicyclo[3.3.0]octan-3-one (55)

The aldehyde (8) (5.527 g) obtained in the usual manner was converted to the corresponding acetal using ethylene glycol (100 ml) and a catalytic amount of p-toluenesulfonic acid in toluene (100 ml). The crude product obtained after the usual work-up was chromatographed on a column of silica gel (hexane/ethyl acetate =½) to give the acetal (55).
Yield: 4.300 g (65.1%).

15-2) Preparation of
(1S,5R,6R,7R)-6-(2,2-ethylenedioxyethyl)-7-hydroxy-2-oxabicyclo[3.3.0]octan-3-one (56)

The acetal (55) (4.180 g) was treated with potassium carbonate (1.18 g) in methanol (100 ml) at room temperature for 2 hours with stirring. The reaction mixture was neutralized with addition of acetic acid, followed by the usual work up to give a crude product. The crude product was chromatographed on a column of silica gel to give the alcohol (56).

Yield: 3.450 g (97.7%).

15-3) Preparation of (1S,5R,6R,7R)-6-(2,2-ethylenedioxyethyl)-7-tetrahydropyranyloxy-2-oxabicyclo[3.3.0]octan-3-one (57)

The alcohol (56) (3.450 g) was converted to the corresponding tetrahydropyranyl ether with dihydropyran (6.9 ml) and a catalitic amount of p-toluenesulfonic acid in dichloromethane (100 ml). The crude product obtained after the usual work-up was chromatographed on a column of silica gel (hexane/ethyl acetate=½) to give the tetrahydropyranyl ether (57).

Yield: 4.701 g (99.6%).

15-4) Preparation of (1S,(3RS),5R,6R,7R)-6-(2,2-ethylenedioxyethyl)-7-tetrahydropyranyloxy-2-oxabicyclo[3.3.0]octan-3-ol (58)

The ether (57) (4.700 g) was reduced in toluene (80 ml) at −78° C. with diisobutylaluminum hydride (1.5-M, 12 ml) to give the lactol (58).

15-5) Preparation of Z-7-[(1R,2R,3R,5S)-2-(2,2-ethylenedioxyethyl)-5-hydroxy-3(tetrahydropyranyloxy)cyclopentyl]hept-5-enoic acid (59)

(4-Carboxybutyl)triphenylphosphonium bromide (22.03 g) and potassium t-butoxide (1-M, 99.4 ml) were treated in THF (100 ml) to give a ylide, to which was added the previously obtained lactol (58) at 0° C., and the mixture was kept at room temperature overnight. The reaction was worked up in the usual manner to give the carboxylic acid (59). ethylenedioxyethyl)-5-hydroxy-3-(tetrahydropyranyloxy)cyclopentyl]hept-5-enoate (60)

The carboxylic acid (59) was treated with diazomethane in ether (150 ml) to give the methyl ester (60). The crude product obtained after the work-up was chromatographed on a column of silica gel (hexane/ethyl acetate =3/2).

Yield: 4.990 g (80.4%; overall for 2 steps).

15-7) Preparation of methyl Z-7-[(1R,2R,3R,5S)-5-t-butyldimethylsiloxy-2-(2,2-ethylenedioxyethyl)-3-(tetrahydropyranyloxy)cyclopentyl]hept-5-enoate (61)

The methyl ester (60) (4.990 g) was converted to the corresponding t-butyldimethylsilyl ether (61). The crude product obtained after the ususal work-up was chromatographed on a column of silica gel (hexane/ethyl acetate =2/1).

Yield: 6.320 g (99.2%).

15-8) Preparation of methyl 7-[(1R,2R,3R,5S)-5-t-butyldimethylsiloxy-2-(2,2-ethylenedioxyethyl)-3(tetrahydropyranyloxy)cyclopentyl]heptanoate (62)

The t-butyldimethylsilyl ester (61) (1.522 g) was hydrogenated with a catalytic amount of 5% palladium on carbon in ethyl acetate (20 ml) and hydrogen gas to give the dihydro compound (62).

Yield: 1.457 g (95.4%).

15-9) Preparation of methyl 7-[(1R,2R,3R,5S)-2-(2,2-ethylenedioxyethyl)-5-hydroxy-3(tetrahydropyranyloxy)cyclopentyl]heptanoate (63)

The dihydro compound (62) (1.400 g) was converted to the alcohol (63) with tetrabutylammonium fluoride (1M, 10 ml) in THF (20 ml).

Yield: 0.7725 g (70.4%).

15-10) Preparation of methyl 7-[(1R,2R,3R,5S)-5-acetoxy-2-(2,2-ethylenedioxyethyl)-3-(tetrahydropyranyloxy)cyclopentyl]heptanoate (64)

The alcohol (63) (0.7725 g) was converted to the corresponding acetate (64) with 4-dimethylaminopyridine and acetic andydride in dichloromethane (10 ml). The crude product obtained after the work-up was chromatographed on a column of silica gel (hexane/ethyl acetate=3/2)

Yield: 0.8484 g (99.7%).

15-11) Preparation of methyl Δ 7-[(1R,2R,3R,5S)-5-acetoxy-2-(2,2-ethylenedioxyethyl)-3-(hydroxy)cyclopentyl]heptanoate (65)

The acetate (64) (0.8400 g) was dissolved in a mixed solvent of acetic acid, THF and water (3/1/1, 20 ml), and the solution was kept at 50° C. for 3 hours. The crude product obtained after the work-up was chromatographed on a column of silica gel (hexane/ethyl acetate =1/1).

Yield: 0.3927 g (55.8%).

15-12) Preparation of methyl 7-[(1R,2R,3R,5S)-5-acetoxy-2-(2-formylmethyl)-5-(hydroxy)cyclopentyl]heptanoate (66)

The alcohol (65) (0.3725 g) was kept in a mixed solvent of acetic acid, THF and water (3/1/1, 10 ml) at 70° C. for 5 hours. The crude product obtained after the work-up was chromatographed on a column of silica gel (hexane/ethyl acetate =3/1).

Yield: 0.3284 g (100%).

15-13) Preparation of methyl 7-[(1R,2R,3R,5S)-5-acetoxy-2-(2-formylmethyl)-5-(tetrahydropyranyloxy)cyclopentyl]heptanoate (67)

The aldehyde (66) (0.3280 g) was converted to the tetrahydropyranyl ether (67) with dihydropyran (0.5 ml)and a catalytic amount of p-toluene-sulfonic acid in dichloromethane (10 ml).

Yield: 0.3772 g (91.5%).

15-14) Preparation of methyl 7-[(1R,2R,3R,5S)-2-(2-formylmethyl)-5-hydroxy-3-(tetrahydropyranyloxy)cyclopentyl]heptanoate (68)

The acetate (67) (0.3772 g) was converted to the corresponding alcohol (68) with potassium carbonate (0.083 g) in methane (10 ml). The crude product obtained after the work-up was chromatographed on a column of silica gel (hexane/ethyl acetate =3/2).

Yield: 0.2485 g (73.4%).

15-15) Preparation of methyl 7-[(1R,2R,3R,5S)-2-(E-5,5-difluoro-4-oxo-2-octenyl)-5-hydroxy-3-(tetrahydropyranyloxy)cyclopentyl]heptanoate (69)

The alcohol (68) (0.2443 g) was treated with dimethyl (3,3-difluoro-2-oxohexyl)phosphonate (0.4915 g), 60% sodium hydride (0.0805 g) and zinc chloride (0.2743 g) in THF (15 ml) to give the α,β-unsaturated ketone (69). The crude product obtained after the work-up was chromatographed on a column of silica gel (hexane/ethyl acetate =2/1).

Yield: 0.1850 g (58.9%).

15-16) Preparation of methyl 7-[(1R,2R,3R,5S)-2-(E-5,5-difluoro-4-oxo-2-octenyl)-5-oxo-3-(tetrahydropyranyloxy)cyclopentyl]heptanoate (70)

The α,β-unsaturated ketone (69) (0.1800 g) was converted to the diketone (70) with Swern oxidation using oxalyl chloride (2-M, 0.42 ml), DMSO (0.12 ml) and triethylamine (0.51 ml) in dichloromethane (8 ml).

Yield: 0.1680 g (93.6%).

15-17) Preparation of methyl 7-[(1R,2R,3R,5S)-2-(E-5,5-difluoro-4-oxo-2-octenyl)-3-hydroxy-5-oxocyclopentyl]heptanoate (71)

The diketone (70) (0.1680 g) was kept in a mixed solvent of acetic acid, THF and water (3/1/1, 20 ml) at 50° C. for 3 hours. The crude product obtained after the work-up was chromatographed on a column of silica gel to give the title compound. (solvent)

Yield: 0.060 g (46.6%).

Compound (71) ($X_1=X_2=F$, $R_2$-$R_3$=propyl, $R'_1$=methyl)

$^1$HMR (CDCl$_3$) δ:0.99 (3H, t, J=7 Hz), 1.1-2.85 (22H, m), 3.67 (3H, s), 4.15 (1H, m), 6.62 (1H, d, J=15 Hz), 7.27 (1H, dt, J=15 Hz, 7.5 Hz)

MS m/z 402 (M+), 384 (M+=H$_2$O), 382 (m+HF), 364 (M+-HFH$_2$O)

What we claim is:

1. A compound of the formula:

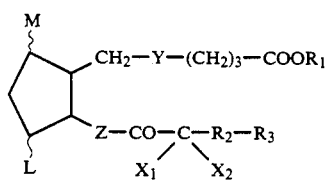
(I)

wherein

L and M are hydrogen atom, hydroxy, lower alkyl, hydroxy(lower)alkyl or oxo, provided that at least one of L and M is not hydrogen atom and that the five-membered ring may have one double bond, and when one of L and M is hydrogen atom and the other of L and M is oxo, then the five-membered ring has one double bond $X_1$ and $X_2$ are hydrogen atom, halogen atom or lower alkyl, Y is —CH$_2$—CH$_2$—, —CH=CH—, —C≡C— or —CO—CH$_2$—, Z is —CH$_2$—CH$_2$—CH$_2$—, —CH=CH—CH$_2$— or —CH$_2$—CH=CH—, $R_1$ is hydrogen atom, lower alkyl, lower cycloalkyl, monocyclic aryl, monocyclic aryl(lower)alkyl or monocyclic aroyl(lower)alkyl, $R_2$ is single bond or lower alkylene, $R_3$ is lower alkyl which is unsubstituted or substituted with halogen, lower cycloalkyl which is unsubstituted or substituted with lower alkyl, monocyclic aryl which is unsubstituted or substituted with halogen or halo(lower)alkyl, or monocyclic aryloxy which is unsubstituted or substituted with halogen or halo(lower)alkyl, or a pharmaceutically acceptable salt when $R_1$ is hydrogen atom.

2. A compound according to claim 1, in which $X_1$ is fluorine atom.

3. A compound according to claim 2, in which $X_2$ is fluorine atom.

4. A compound according to claim 1, in which Y is —CH=CH.

5. A compound according to claim 1, in which Z is —CH$_2$—CH$_2$—CH$_2$—.

6. A compound according to claim 1, in which $R_2$ is single bond and $R_3$ is lower alkyl.

7. A compound according to claim 1, in which L and M are hydrogen atom, hydroxy or oxo and the five-membered ring may have one double bond, $X_1$ and $X_2$ are hydrogen atom, fluorine atom or methyl, Y is —CH$_2$ —CH$_2$ —, —CH=CH—, —C≡C— or —CO—CH$_2$ —, Z is —CH$_2$ —CH$_2$ —CH$_2$ — or —CH=CH—CH$_2$ —, $R_1$ is hydrogen atom, methyl, ethyl, isopropyl, benzyl or phenacyl, and $R_2$-$R_3$ is butyl or hexyl.

8. A compound according to claim 1, in which the compound is 15-dehydroxy-17,17-difluoro-13,14-dihydro-16-oxo-PGE$_1$ or its lower alkyl ester.

9. A compound according to claim 1, in which the compound is 15-dehydroxy-17,17-difluoro-13,14-dihydro-14,15-dehydro-16-oxo-PGE$_1$ or its lower alkyl ester.

10. A compound accroding to claim 1, in which the compound is 15-dehydroxy-17,17-difluoro-13,14-dihydro-16-oxo-PGE$_2$ or its lower alkyl ester.

11. A compound accroding to claim 1, in which the compound is 15-dehydroxy-17,17-difluoro-13,14-dihydro-20-methyl-16-oxo-PGE$_2$ or its lower alkyl ester.

12. A compound according to claim 1, in which the compound is 15-dehydroxy-17,17-difluoro-13,14-dihydro-16-oxo-PGA$_2$ or its lower alkyl ester.

13. A compound according to claim 1, in which the compound is 15-dehydroxy-17,17-difluoro-13,14-dihydro-16-oxo-PGD$_2$ or its lower alkyl ester.

14. A compound according to claim 1, in which the compound is 15-dehydroxy-17,17-difluoro-13,14-dihydro-16-oxo-PGF$_{2\alpha}$ or its lower alkyl ester.

* * * * *